(12) United States Patent
Jani et al.

(10) Patent No.: US 8,523,911 B2
(45) Date of Patent: Sep. 3, 2013

(54) TRANSVERSE CONNECTOR INCLUDING LOCKING CAP WITH BEARING SURFACE

(75) Inventors: Mehul R. Jani, Audubon, PA (US); Michal Zentko, Lansdale, PA (US)

(73) Assignee: Globus Medical, Inc., Audubon, PA (US)

( * ) Notice: Subject to any disclaimer, the term of this patent is extended or adjusted under 35 U.S.C. 154(b) by 78 days.

(21) Appl. No.: 12/883,903

(22) Filed: Sep. 16, 2010

(65) Prior Publication Data

US 2012/0071926 A1 Mar. 22, 2012

(51) Int. Cl.
*A61B 17/70* (2006.01)

(52) U.S. Cl.
USPC .......... 606/250; 606/270; 606/271; 606/272; 606/264

(58) Field of Classification Search
USPC .................................. 606/250–279
See application file for complete search history.

(56) References Cited

U.S. PATENT DOCUMENTS

| | | | | |
|---|---|---|---|---|
| 4,932,975 A * | 6/1990 | Main et al. | ............... | 623/17.12 |
| 5,108,395 A * | 4/1992 | Laurain | ..................... | 606/86 B |
| 5,549,607 A * | 8/1996 | Olson et al. | ................. | 606/251 |
| 5,688,272 A * | 11/1997 | Montague et al. | ............ | 606/252 |
| 6,090,111 A | 7/2000 | Nichols | | |
| 6,302,883 B1 * | 10/2001 | Bono | .......................... | 606/291 |
| 6,565,565 B1 | 5/2003 | Yuan | | |
| 6,669,729 B2 | 12/2003 | Chin | | |
| 6,740,086 B2 | 5/2004 | Richelsoph | | |
| 6,755,829 B1 | 6/2004 | Bono | | |
| 6,786,903 B2 | 9/2004 | Lin | | |
| 7,081,117 B2 * | 7/2006 | Bono et al. | .................... | 606/300 |
| 7,125,426 B2 | 10/2006 | Moumene | | |
| 7,141,051 B2 * | 11/2006 | Janowski et al. | ............. | 606/272 |
| 7,261,714 B2 | 8/2007 | Richelsoph | | |
| 7,282,064 B2 | 10/2007 | Chin | | |
| 7,645,294 B2 * | 1/2010 | Kalfas et al. | .................. | 606/250 |
| 7,837,714 B2 * | 11/2010 | Drewry et al. | ................ | 606/250 |
| 7,909,856 B2 * | 3/2011 | Yuan et al. | .................... | 606/279 |
| 8,257,399 B2 * | 9/2012 | Biedermann et al. | ......... | 606/265 |
| 2002/0120272 A1 * | 8/2002 | Yuan et al. | ..................... | 606/61 |
| 2004/0153068 A1 * | 8/2004 | Janowski et al. | .............. | 606/61 |
| 2005/0119657 A1 | 6/2005 | Goldsmith | | |
| 2005/0228326 A1 * | 10/2005 | Kalfas et al. | ................... | 602/19 |
| 2006/0200128 A1 * | 9/2006 | Mueller | ......................... | 606/61 |
| 2007/0299446 A1 | 12/2007 | Chin | | |
| 2008/0045955 A1 | 2/2008 | Berrevoets | | |
| 2009/0177234 A1 * | 7/2009 | Butler et al. | ................... | 606/277 |
| 2010/0087864 A1 * | 4/2010 | Klein et al. | .................... | 606/264 |

(Continued)

FOREIGN PATENT DOCUMENTS

WO   WO 2008039777 A2 *   4/2008

*Primary Examiner* — Jan Christopher Merene

(57) ABSTRACT

The present invention provides a spine stabilization system having a first bone anchor having a first receiving portion and a second bone anchor having a second receiving portion. The first and second elongated rods are positioned within the first and second receiving portions. The first and second locking caps are configured to retain and capture the first and second elongated rods within the first and second bone anchors. The top connector is configured with a first and a second end, which are provided with elongated openings. The first and second locking caps have a threaded portion for coupling to a first and second locking nut. The locking caps are also provided with at least one flange for coupling to the bone anchor, and a bearing surface spaced apart from the bone anchor, the bearing surface configured to contact the top connector.

14 Claims, 4 Drawing Sheets

(56) References Cited

U.S. PATENT DOCUMENTS

2010/0087867 A1* 4/2010 Klein et al. .................. 606/278
2010/0094345 A1* 4/2010 Saidha et al. ................ 606/250
2012/0065686 A1* 3/2012 Black et al. .................. 606/252

* cited by examiner

TRANSVERSE CONNECTOR INCLUDING LOCKING CAP WITH BEARING SURFACE

CROSS-REFERENCE TO RELATED APPLICATIONS

The present application claims priority to U.S. Provisional Application 61/243,642 filed on Sep. 18, 2009. All publications and patent applications mentioned in this specification are herein incorporated by reference to the same extent as if each individual publication or patent application was specifically and individually indicated to be incorporated by reference.

FIELD OF THE INVENTION

The present invention relates to a device which stabilizes the spine. In particular, the present invention is related to stabilizing the spine through the use of rods and rod connectors.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment for these spinal irregularities often involves using a system of pedicle screws and rods to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. Surgeons utilize polyaxial bone screws throughout the spine for posterior fusion. The rigidity or stiffness of posterior fusion systems is commonly augmented by the use of trans-connectors or t-connectors. The screw trajectory and placement is often dictated by the natural anatomy and frequently results in situations where the polyaxial bone screws are very close or even touch the adjacent screws.

In the abovementioned situation, a standard t-connector or trans-connector that affixes directly onto the titanium alloy rods may not be suitable due to the proximity of the bone screws. There is a need for a transverse connector which would be ideally suited to provide rigidity to the construct by attaching to the heads or "tulips" of the opposing polyaxial bone screws.

SUMMARY OF THE INVENTION

The present invention provides a spine stabilization system having a first bone anchor having a first receiving portion and a second bone anchor having a second receiving portion. The first and second elongated rods are positioned within the first and second receiving portions. The first and second locking cap are configured to retain and capture the first and second elongated rods within the first and second bone anchors. The top connector is configured with a first and second end, and the first and second ends are provided with an elongated opening. The first and second locking nut lock the top connector to the first and second bone anchors. The first and second locking caps have a threaded portion for coupling to the first and second locking nut. The locking caps are also provided with at least one flange for coupling to the bone anchor, and a bearing surface spaced apart from the bone anchor, the bearing surface configured to contact the top connector.

BRIEF DESCRIPTION OF THE DRAWINGS

The attached drawings illustrate the elements of the present invention. Design and utility features of the present invention are also disclosed.

DETAILED DESCRIPTION OF THE INVENTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to limit the scope of the disclosure, including the claims, is limited to that embodiment.

Figure 1:
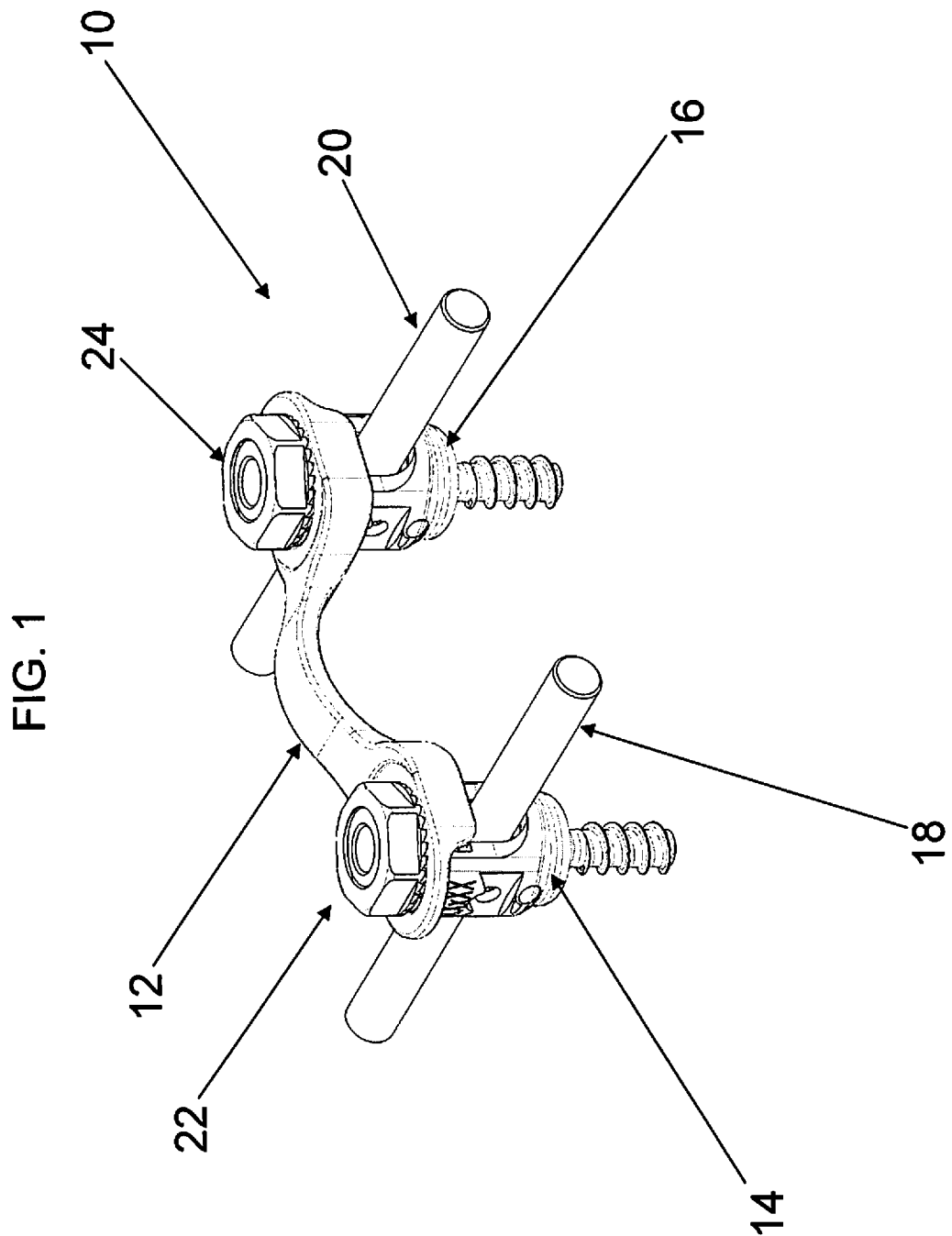
FIG. 1 illustrates a spine stabilization system according to the present invention.

FIG. 1 illustrates a spine stabilization system 10 according to a preferred embodiment of the present invention. The system 10 comprises a top connector 12, at least two bone anchors 14, 16, and elongated rods 18, 20 that are captured within a portion of the bone anchors 14, 16. The system 10 also comprises locking nuts 22, 24 which secure the top connector 12 to the bone anchors 14, 16.

It should be noted that although in the preferred embodiment, a polyaxial screw is shown as a bone anchor, each bone anchor may have any configuration that may be used with a spinal stabilization system such as elongated rods, monoaxial screws, bolts, hooks or any other implant or combination of implants designed to engage bone and connect to a spinal fixation element.

Figure 2:
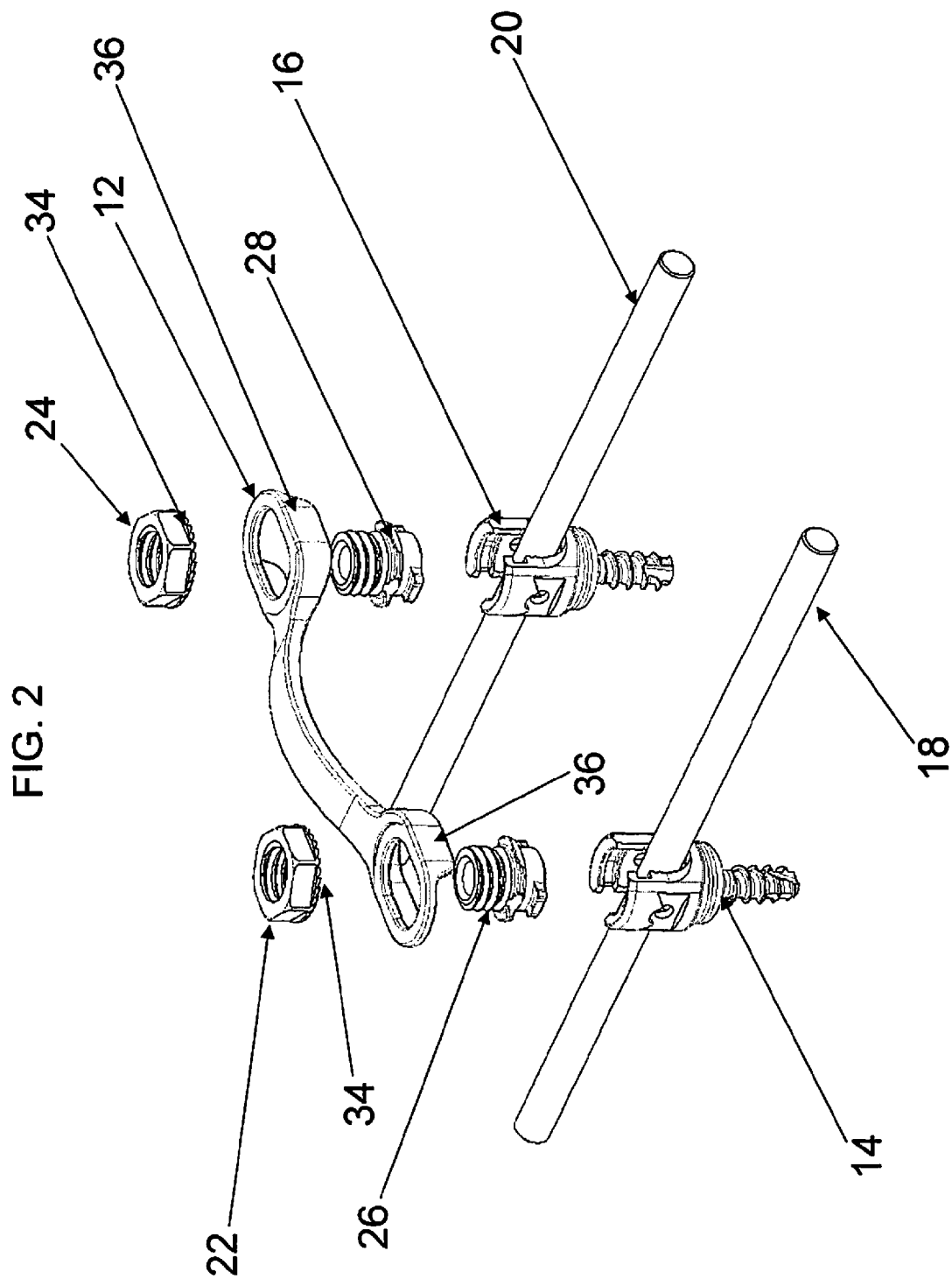
FIG. 2 illustrates an exploded view of the spine stabilization system of the present invention.

Now turning to FIG. 2, an exploded view of system 10 is shown. As illustrated in FIG. 2, the elongated rods 18, 20 are positioned within the tulip portions of the bone anchors 14, 16. The locking caps 26, 28 are then used to capture and retain the elongated rods within the tulip portion of the bone anchors 14, 16. The locking caps will be discussed in greater detail with reference to FIGS. 3-5.

In a preferred embodiment, the top connector 12 may include elongated openings 30, 32 through which the first end of the locking caps 26, 28 extend. The elongated openings 30, 32 allow the locking caps 26, 28 and consequently the polyaxial bone anchors 14, 16 to translate medial-laterally in the elongated openings 30, 32 before they are locked in the desired position. The locking caps 26, 28 are locked in place on the top connector 12 via the locking nuts 22, 24 which threadingly engages the threaded portion of the locking caps 26, 28. In a preferred embodiment, the locking nuts 22, 24 may include a series of serrations 34 oriented to prevent the locking nuts 22, 24 from unthreading when exposed to micromotions. In another embodiment, the locking nuts 22, 24 may include a cut in the internal threading to lock the nuts 22, 24 in place once it is installed.

As seen herein, the top connector also includes a lip 36 on opposing portions of the top connector 12 that extends downwardly from the top surface of the top connector and partially surrounding the elongated opening. The lip 36 serves an important function as it counters the rotation of one bone anchor with respect to the bone anchor on the contra-lateral side. In addition, the lip 36 provides additional bearing or engagement surfaces for augmenting the fixation of the bone anchors to the top connector.

Figure 3:
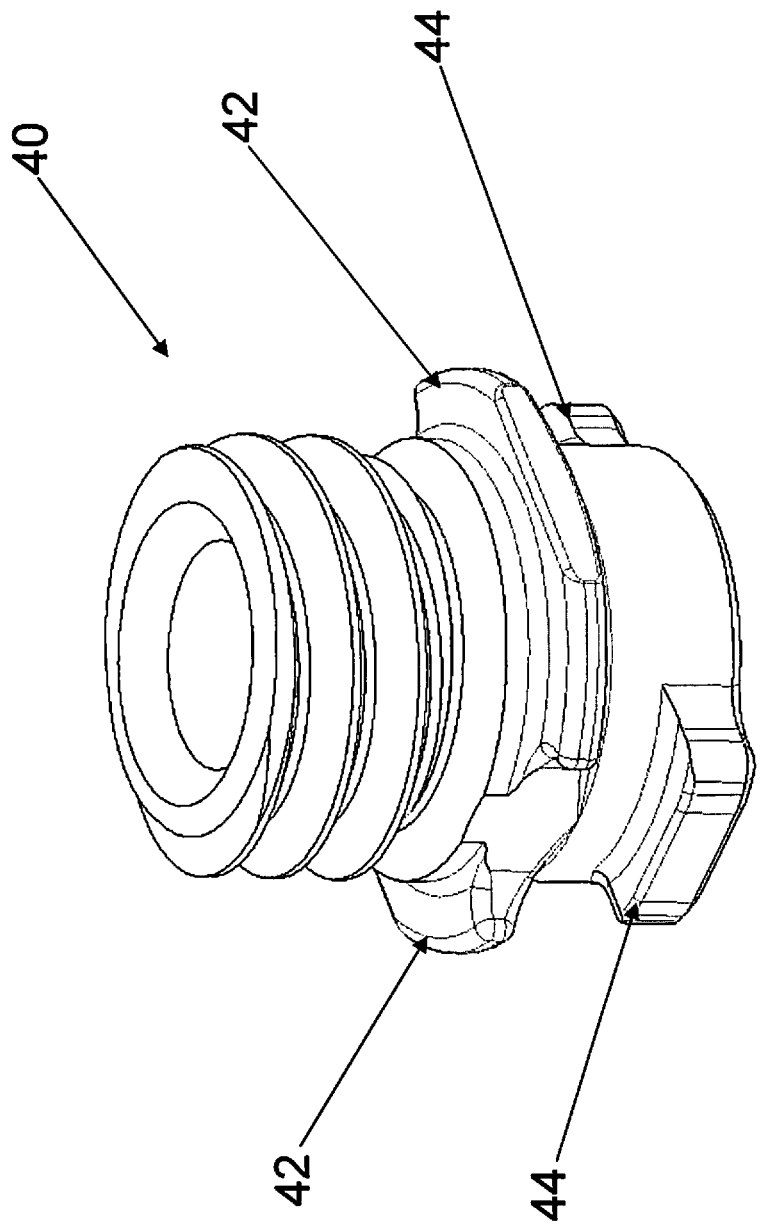
FIG. 3 illustrates an exemplary embodiment of a locking cap according to the present invention.

The top connector 12 as illustrated in FIGS. 1-3 may be configured in a variety of a different ways, for instance, the top connector 12 may be configured with a radius of curvature and be shaped in any form that spans the vertebra. The top connector 12 is composed of titanium material but it not limited to this material. The connector 12 may be composed of any bio-compatible material such as PEEK. Also, the connector 12 is configured to have a thickness that is optimal for inter-operative contouring to accommodate for a patient's anatomy.

The elongated openings 30, 32 in the preferred embodiment are elliptical in configuration. However, the openings 30, 32 may be configured in any shape or form to enable a portion of a locking cap 40 to extend through.

Figure 5:
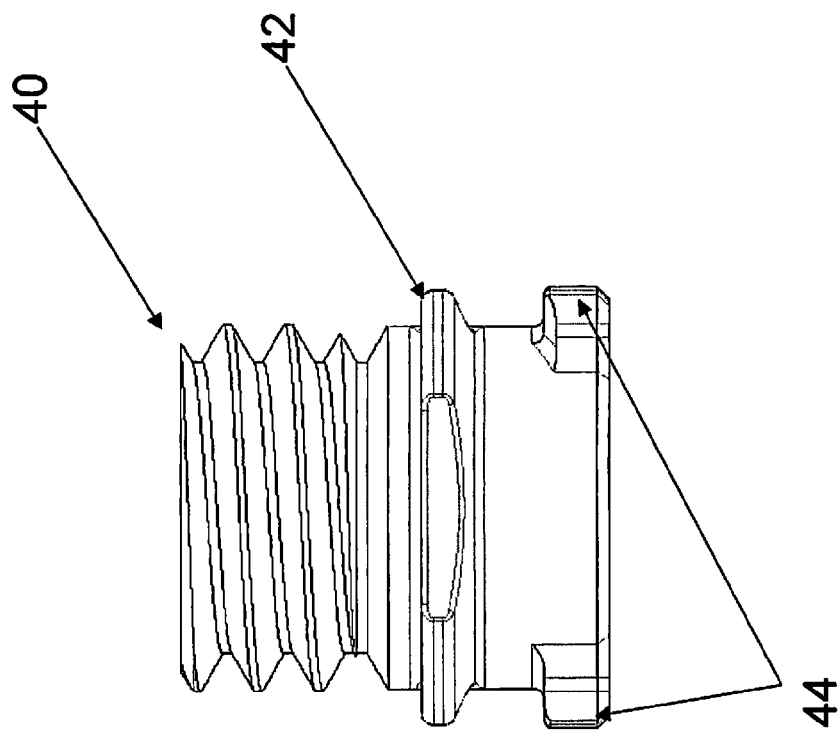
FIGS. 4 and 5 illustrate a front and side view of the locking cap shown in FIG. 3.
Figure 4:
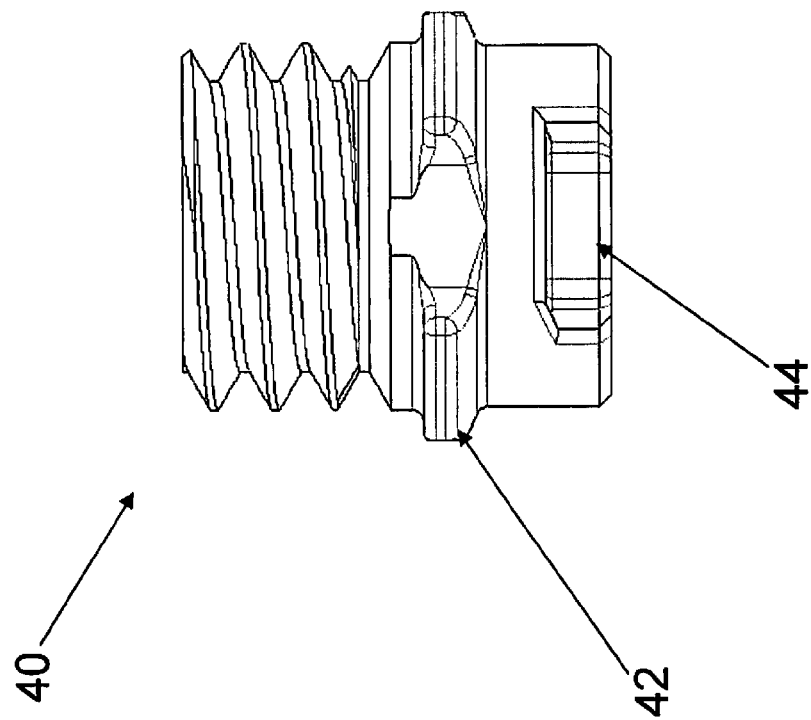

Now turning to FIGS. 3-5, a more detailed illustration of a locking cap 40 according to a preferred embodiment of the present invention is shown. The locking cap 40 preferably includes a threaded portion having external threading, a middle portion having a contact bearing surface 42 and a flange portion having opposed flanges 44. The flanges 44 are configured and dimensioned to fit within two grooves located on the inside of the tulip of the bone anchor. The contact bearing surface 42, although configured and dimensioned as a ledge extending around the circumference of the locking hap, any configuration for contacting and supporting the top connector would be suitable. For instance, the ledge may be separated into multiple parts surrounding the locking cap or a ledge having various geometric shapes that are optimal for supporting the top connector. The contact bearing surface 42 receives the top connector rather than having pressure from the top connector be applied directly to the top of the tulip portion of the bone anchor.

As shown in FIGS. 4 and 5, the contact bearing surface 42 is positioned between the external threaded portion of the locking cap and flange portion 44 of the locking cap 40. In the preferred embodiment, the contact bearing surface 42 is slightly positioned above the flange portion of the locking cap 40, however any configuration may be utilized whereby the a portion of the top connector connects the contact bearing surface 42. For instance, the positioning of the contact bearing surface 42 as well as the width and thickness of the surface 42 may be adapted to various types of bone anchors.

In another embodiment, the contact bearing surface 42 may have indents or ridges that correspond to matching ridges or indents on the bottom surface of the top connector to provide better contact. The contact bearing surface 42 has a width that is greater than the width of the flange portion and the thread portion of the locking cap. The contact bearing surface 42 is also configured with a thickness for supporting the top connector.

It should be noted that although in the preferred embodiment, the locking cap has a top portion that is threaded, the present invention is limited to this embodiment. For instance, the top portion of the locking cap may be configured as any mechanical structure for receiving the top connector. The locking cap can be configured to have a dove tail connect to the locking apparatus which locks the top connector to the bone anchor. Thus various connection methods may be used to lock the top connector to the bone anchor.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A spine stabilization system comprising:
   a first bone anchor having a first receiving portion and a second bone anchor having a second receiving portion;
   a first and second elongated rod positioned within the first and second receiving portions respectfully;
   a first and second locking cap configured to retain and capture the first and second elongated rods within the first and second bone anchors;
   a top connector having first and second ends, the first end and the second end having elongated openings;
   a first and a second locking nut for coupling the top connector to the first and second bone anchors, wherein the first and second locking nut each include serrations that bear down on an upper surface of the top connector;
   wherein each of the first and second locking caps further comprises:
     a threaded portion for coupling to the first or second locking nut,
     at least one flange portion for coupling to the bone anchor, and
     a bearing surface, wherein the bearing surface of the first locking cap is spaced apart from the first bone anchor and the bearing surface of the second locking cap is spaced apart from the second bone anchor, the bearing surface contacting the top connector, wherein the bearing surface is positioned between the threaded portion and the flange portion, wherein between the bearing surface and the flange portion the locking cap is non-threaded, and wherein the bearing surface has a width that is greater than the width of the flange portion and the threaded portion, wherein the bearing surface is positioned adjacent to and closer to the threaded portion than the at least one flange portion.

2. The spine stabilization system according to claim 1, wherein the top connector is comprised of PEEK.

3. The spine stabilization system according to claim 1, wherein the first and second locking nuts comprise a plurality of serrations.

4. The spine stabilization system according to claim 1, wherein the first and second bone anchors comprise a first and second rod receiving portions.

5. The spine stabilization system according to claim 1, wherein the first and second receiving portions are configured with a first and second flange receiving portion.

6. The spine stabilization system according to claim 1, wherein the top connector is configured with a lip on the first and second ends of the top connector.

7. The spine stabilization system according to claim 1, wherein the locking caps and consequently the bone anchors are adapted to translate medial-laterally in the elongated openings before they are locked in the desired position.

8. The spine stabilization system according to claim 4, wherein the bearing surface of the first and second locking caps spaced apart from an upper portion of the first and second rod receiving portions.

9. A method for stabilizing a posterior rod construct in a spine of an animal comprising the steps of:
- positioning a first bone anchor having a first receiving portion and a second bone anchor having a second receiving portion in a portion of a spine;
- positioning a first and a second elongated rod within the first and second receiving portions of the first and second bone anchors respectfully;
- positioning a first and second locking cap to retain and capture the first and second elongated rods within the first and second bone anchors;
- placing a top connector having a first and second end, the first and second end having an elongated opening;
- positioning a first and a second locking nut for coupling the top connector to the first and second bone anchors, wherein the first and second locking nut each include serrations that bear down on an upper surface of the top connector;
- wherein the first and second locking caps further comprise:
  - a threaded portion for coupling to the first or second locking nut,
  - at least one flange for coupling to the bone anchor, and
  - a bearing surface, wherein the bearing surface of the first locking cap is spaced apart from the first bone anchor and the bearing surface of the second locking cap is spaced apart from the second bone anchor, wherein the bearing surface is positioned between the threaded portion and the flange, wherein between the bearing surface and the flange the locking cap is non-threaded, and wherein the bearing surface has a width that is greater than the width of the flange and the threaded portion
- wherein the placing of the top connector further comprises the step of positioning bottom surfaces of the top connector on the bearing surface of the first and second locking cap, wherein the bearing surface is positioned adjacent to and closer to the threaded portion.

10. The method according to claim 9, wherein method further comprises creating an access path for positioning the posterior rod construct.

11. The method according to claim 9, wherein the method further comprises tightening the first and second locking nuts so a plurality of serrations engages an upper portion of the top connector.

12. The method according to claim 9, wherein the method further comprises tightening the first and second locking caps on the upper portion of the bone anchor by turning the first and second locking caps so that the flange portion of the first and second locking caps engage with the first and second flange receiving portion of the bone anchors.

13. The method according to claim 9, wherein the method further comprises contacting a lip portion of the first end of the top connector with a side portion of the first bone anchor.

14. The method according to claim 9, wherein the method further comprises translating the first and seconds locking caps and the first and second bone anchors medial-laterally in the elongated openings before they are locked in the desired position.

* * * * *